(12) United States Patent
Dastgheib et al.

(10) Patent No.: US 9,030,239 B1
(45) Date of Patent: May 12, 2015

(54) SIGMA-DELTA ANALOG-TO-DIGITAL CONVERTER

(71) Applicant: Google Inc., Mountain View, CA (US)

(72) Inventors: Alireza Dastgheib, Mountain View, CA (US); Brian Otis, Sunnyvale, CA (US)

(73) Assignee: Google Inc., Mountain View, CA (US)

( * ) Notice: Subject to any disclaimer, the term of this patent is extended or adjusted under 35 U.S.C. 154(b) by 3 days.

(21) Appl. No.: 14/143,024

(22) Filed: Dec. 30, 2013

(51) Int. Cl.
*G05F 3/02* (2006.01)
*G01N 27/48* (2006.01)
*G01N 27/00* (2006.01)

(52) U.S. Cl.
CPC *G05F 3/02* (2013.01); *G01N 27/48* (2013.01); *G01N 27/002* (2013.01); *G01N 27/00* (2013.01)

(58) Field of Classification Search
CPC ...... G01N 27/00; G01N 27/002; G01N 27/48
USPC ......... 327/540, 130, 131, 132, 134, 135, 137, 327/140, 164, 165, 166, 170, 172, 175, 538, 327/541, 543, 548
See application file for complete search history.

(56) References Cited

U.S. PATENT DOCUMENTS

| | | | |
|---|---|---|---|
| 6,621,767 B1 * | 9/2003 | Kattan | 368/113 |
| 2010/0066378 A1 * | 3/2010 | Ahmadi et al. | 324/429 |
| 2011/0121819 A1 | 5/2011 | Minch et al. | |
| 2012/0205258 A1 | 8/2012 | Noble et al. | |

OTHER PUBLICATIONS

Gore et al., "A Multichannel Femtoampere-Sensitivity Potentiostat Array for Biosensing Applications," IEEE Transactions on Circuits and Systems -I: Regular Papers, Nov. 2006, pp. 2357-2363, vol. 53, No. 11.
Stanaćević et al., "VLSI Potentiostat Array With Oversampling Gain Modulation for Wide-Range Neurotransmitter Sensing," IEEE Transactions on Biomedical Circuits and Systems, Mar. 2007, pp. 63-72, vol. 1, No. 1.

* cited by examiner

*Primary Examiner* — Jung Kim
(74) *Attorney, Agent, or Firm* — McDonnell Boehnen Hulbert & Berghoff LLP

(57) ABSTRACT

A potentiostat includes a voltage regulator, a current mirror, a capacitor, a comparator, a current source, and a counter. The voltage regulator maintains a voltage on a working electrode of an electrochemical sensor. The current mirror develops a mirror current that mirrors an input current from the working electrode. The capacitor is alternately charged by the mirror current, causing the capacitor voltage to increase at a rate related to the current's magnitude, and discharged by a control current, causing the capacitor voltage to decrease. The comparator outputs a waveform that includes upward and downward transitions based on the variations of the capacitor voltage. The current source produces the control current based on the waveform. The counter counts the number of upward or downward transitions in the waveform during a predetermined sampling period to produce a digital output. The digital output is representative of the magnitude of the input current.

10 Claims, 7 Drawing Sheets

SIGMA-DELTA ANALOG-TO-DIGITAL CONVERTER

BACKGROUND

Unless otherwise indicated herein, the materials described in this section are not prior art to the claims in this application and are not admitted to be prior art by inclusion in this section.

An electrochemical amperometric sensor can measure a concentration of an analyte by measuring a current through a working electrode that is generated by electrochemical oxidation or reduction reactions related to the analyte. A reduction reaction occurs when electrons are transferred from the electrode, whereas an oxidation reaction occurs when electrons are transferred to the electrode. The direction of the electron transfer is dependent upon a voltage applied to the working electrode. At least one other electrode (e.g., a counter electrode, a reference electrode) can complete the circuit. When the working electrode is appropriately biased, the output current can be proportional to the reaction rate, which can provide a measure of the concentration of the analyte surrounding the working electrode.

A potentiostat may be configured to apply a voltage to the working electrode, relative to the reference electrode, and measure the current through the working electrode, such that the current is related to the concentration of the analyte. In some examples, the potentiostat may include an analog-to-digital converter (ADC) that provides a digital output that is representative of the current through the working electrode. In a conventional approach, the input current is integrated by an active integrator to provide a ramp voltage. However, the arrangement of the electrodes in an electrochemical sensor can result in a relatively high capacitance at the input of the active integrator. Operating the active integrator with such high input capacitance may result in high power consumption by the active components.

SUMMARY

In one aspect, the present disclosure provides a system. The system includes a working electrode of an electrochemical sensor, a current mirror, a voltage regulator, a current source, a capacitor, a comparator, and a counter. The working electrode is configured to develop an input current. The current mirror is coupled to the working electrode and is configured to develop a mirror current that mirrors the input current. The voltage regulator is coupled to the working electrode and current mirror, and is configured to maintain a voltage on the working electrode based on a reference voltage. The current source is configured to develop a control current. The capacitor is coupled to the current mirror and current source, and is configured to develop a capacitor voltage in response to at least the mirror current and control current. The comparator is coupled to the capacitor and is configured to output a waveform based on variations of the capacitor voltage relative to a comparison voltage. The counter is coupled to the comparator. The counter is configured to detect a particular feature in the waveform output from the comparator and to provide a digital output based on a number of times the particular feature in the waveform occurs during a predetermined sampling period.

In another aspect, the present disclosure provides a method. An input current from a working electrode of an electrochemical sensor is received by a current mirror. A mirror current that mirrors the input current is developed by the current mirror. A control current is provided by a current source based on a waveform. A capacitor voltage is developed by a capacitor in response to at least the mirror current and control current. The waveform is generated by a comparator based on variations of the capacitor voltage relative to a comparison voltage. A digital output is provided by a counter based on a number of times a particular feature in the waveform occurs during a predetermined sampling period.

In another aspect, the present disclosure provides a system that includes: (1) means for developing a mirror current that mirrors an input current from a working electrode of an electrochemical sensor; (2) means for providing a control current based on a waveform; (3) means for developing a capacitor voltage in response to at least the mirror current and control current; (4) means for generating the waveform based on variations of the capacitor voltage relative to a comparison voltage; and (5) means for providing a digital output based on a number of times a particular feature in the waveform occurs during a predetermined sampling period.

These as well as other aspects, advantages, and alternatives, will become apparent to those of ordinary skill in the art by reading the following detailed description, with reference where appropriate to the accompanying drawings.

DETAILED DESCRIPTION

I. Overview

Figure 1:
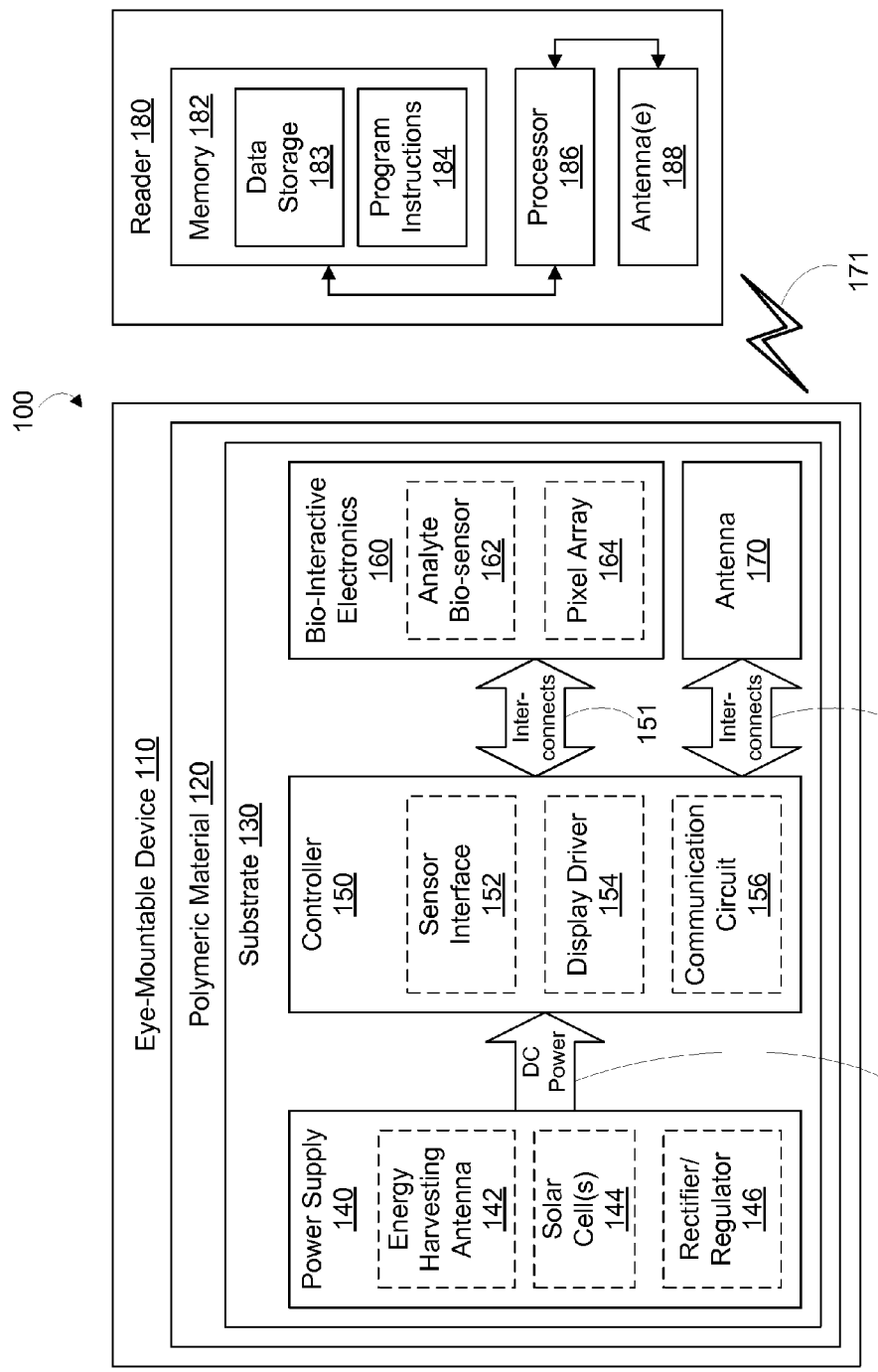
FIG. 1 is a block diagram of an example system that includes an eye-mountable device in wireless communication with a reader, in accordance with an example embodiment.

An electrochemical sensor may be used to detect an analyte in a fluid by measuring a current related to oxidation or reduction of the analyte or a product of a reaction involving the analyte. The electrochemical sensor could include a working electrode and a counter electrode. The oxidation or reduction reaction may occur when an appropriate voltage is applied to the working electrode relative to a reference electrode. The current related to oxidation or reaction may be measured through the working electrode. In some examples, the measured current can be related to a concentration of the analyte in the fluid.

A potentiostat may be used to apply the appropriate voltage to the working electrode and measure the current through the working electrode. In an example, the current through the working electrode (input current) flows through a current mirror, and the current mirror develops a mirror current that mirrors (e.g., replicates) the input current. In such examples, the mirror current can be measured instead of measuring the input current directly, thereby beneficially avoiding the capacitance associated with the working electrode.

To measure the mirror current, a passive integrator (e.g., a capacitor) under control of a sigma-delta ADC may be used. For example, a current source in the sigma-delta ADC may modulate a control current so that the capacitor is alternately (i) charged by the mirror current, to develop a voltage that increases at a rate related to the magnitude of the mirror current, and (ii) discharged by the control current. A comparator may output a waveform based on variations of the capacitor voltage relative to a comparison voltage. The current source may modulate the control current based on the waveform. A counter in the sigma-delta ADC may count the number of upward or downward transitions in the waveform occurring during a predetermined sampling period to develop a digital output. The digital output is representative of the magnitude of the mirror current and, hence, the input current from the working electrode.

The fluid containing the analyte could be a body fluid, such as tear fluid, blood, saliva, sweat, urine, etc. Such body fluids may include inorganic electrolytes (e.g., $Ca^{2+}$, $Mg^{2+}$, $Cl^-$), organic components (e.g., glucose, lactate, proteins, lipids, etc.), or other components that can be used to diagnose health states. To sense an analyte in a body fluid, the electrochemical sensor could be provided in a body-mountable device, such as an eye-mountable device, tooth-mountable device, or skin-mountable device, that can be mounted at a location where the electrochemical sensor can be exposed to the body fluid. The potentiostat for the electrochemical sensor could also be included in the body-mountable device.

In a specific example, the electrochemical sensor and potentiostat could be included in an eye-mountable device and configured to sense an analyte (e.g., glucose) in tear fluid. The eye-mountable device may include a substrate on which an electrochemical sensor (including a working electrode, reference electrode, and reagent layer), antenna, potentiostat, and other electronics are mounted. The substrate and components mounted thereon may be at least partially embedded in a polymeric material. The polymeric material may include a channel through which tear fluid may reach the electrochemical sensor. With this configuration, the potentiostat in the eye-mountable device may be used to measure the current through the working electrode of the electrochemical sensor, and the measurements may be communicated wirelessly using the antenna.

In some examples, the polymeric material can be in the form of a round lens (e.g., similar to a contact lens) with a concave curvature configured to mount to a corneal surface of an eye. The substrate can be embedded near the periphery of the polymeric material to avoid interference with vision. The electrochemical sensor can be arranged on the substrate to face inward, toward the corneal surface, so as to generate clinically relevant readings from near the surface of the cornea and/or from tear fluid interposed between the polymeric material and the corneal surface. Additionally or alternatively, the electrochemical sensor can be arranged on the substrate to face outward, away from the corneal surface and toward the layer of tear fluid coating the surface of the polymeric material exposed to the atmosphere.

An external reader device or "reader" can radiate radio frequency (RF) radiation to power the eye-mountable device. In some examples, the reader can operate to intermittently interrogate the eye-mountable device to measure the analyte by radiating sufficient RF power to enable the eye-mountable device to obtain a measurement and communicate the measurement using the antenna. The reader can also store the measurements communicated by the eye-mountable device. In this way, the reader can acquire a series of analyte concentration measurements over time without continuously powering the eye-mountable device.

In some examples, the electrochemical sensor and potentiostat may be included in a body-mountable device to measure an analyte in a body fluid. In other examples, the electrochemical sensor and potentiostat may be included in a device to measure an analyte in some other type of fluid. For example, the device may be used to measure an analyte related to water quality in a swimming pool, water treatment plant, etc. Other examples are possible as well.

II. Example Eye-Mountable Devices

FIG. 1 is a block diagram of a system 100 that includes an eye-mountable device 110 in wireless communication with a reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some embodiments, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

The substrate 130 can be ring-shaped with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can have a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOx") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

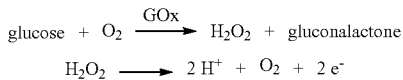

$$\text{glucose} + O_2 \xrightarrow{\text{GOx}} H_2O_2 + \text{gluconalactone}$$
$$H_2O_2 \longrightarrow 2H^+ + O_2 + 2e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The reader 180 can be configured to be external to the eye; i.e., is not part of the eye-mountable device. Reader 180 can include one or more antennae 188 to send and receive wireless signals 171 to and from the eye-mountable device 110. In some embodiments, reader 180 can communicate using hardware and/or software operating according to one or more standards, such as, but not limited to, a RFID standard, a Bluetooth standard, a Wi-Fi standard, a Zigbee standard, etc.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or reader 180), etc. The memory 182 can also include program instructions 184 for execution by the processor 186 to cause the reader 180 to perform processes specified by the instructions 184. For example, the program instructions 184 can cause reader 180 to provide a user interface that allows for retrieving information communicated from the eye-mountable device 110 (e.g., sensor outputs from the analyte bio-sensor 162). The reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

In some embodiments, reader 180 can be a smart phone, digital assistant, or other portable computing device with wireless connectivity sufficient to provide the wireless communication link 171. In other embodiments, reader 180 can be implemented as an antenna module that can be plugged in to a portable computing device; e.g., in scenarios where the communication link 171 operates at carrier frequencies not commonly employed in portable computing devices. In even other embodiments discussed below in more detail in the context of at least FIG. 5, the reader 180 can be a special-purpose device configured to be worn relatively near a wearer's eye to allow the wireless communication link 171 to operate with a low power budget. For example, the reader 180 can be integrated in eyeglasses, integrated in a piece of jewelry such as a necklace, earring, etc., or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the reader 180 (e.g., via the communication circuit 156). The sensor reading can be communicated by, for example, modulating an impedance of the communication antenna 170 such that the modulation in impedance is detected by the reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the reader 180 can accumulate a set of analyte concentration measurements over time without continuously powering the eye-mountable device 110.

Figure 2A:
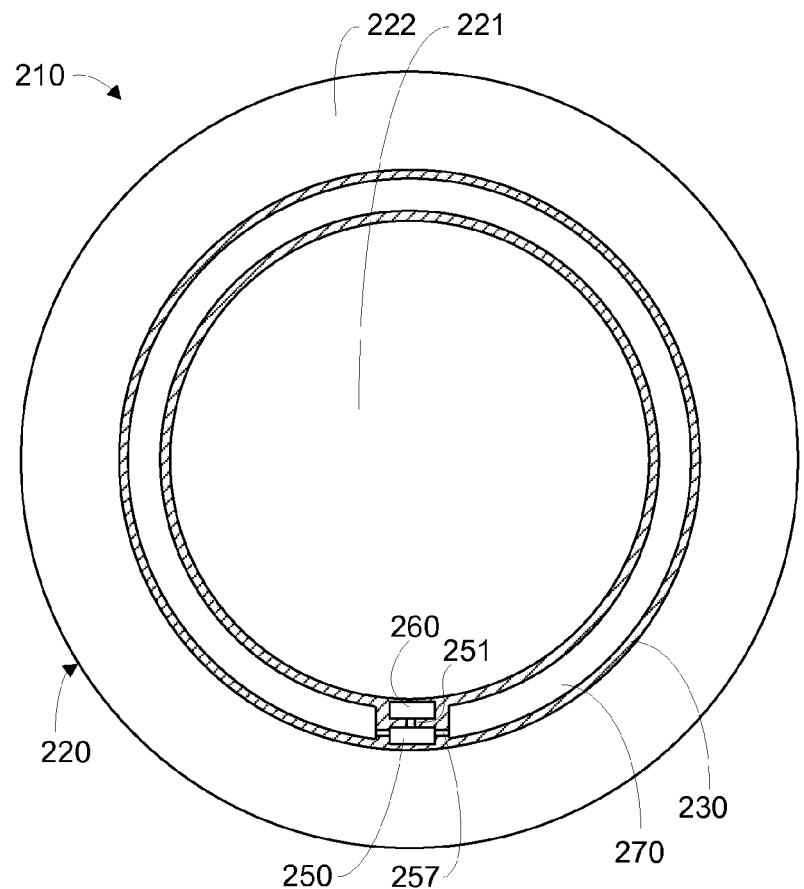
FIG. 2A is a bottom view of an example eye-mountable device, in accordance with an example embodiment.
Figure 2B:
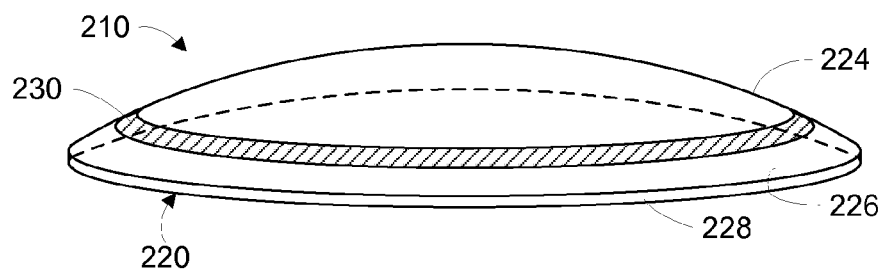
FIG. 2B is a side view of the example eye-mountable device shown in FIG. 2A, in accordance with an example embodiment.

FIG. 2A is a bottom view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. In some embodiments, eye-mountable device 210 can include some or all of the above-mentioned aspects of eye-mountable device 110. In other embodiments, eye-mountable device 110 can further include some or all of the herein-mentioned aspects of eye-mountable device 210.

The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the convex surface 224 of the eye-mountable device 210, bio-interactive electronics 260 is mounted to a side of the substrate 230 facing the convex surface 224. Where the bio-interactive electronics 260 includes an analyte bio-sensor, for example, mounting such a bio-sensor on the substrate 230 facing the convex surface 224 allows the bio-sensor to sense analyte concentrations in tear film through channel 272 (shown in FIGS. 2C and 2D) in the polymeric material 220 to convex surface 224. In some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instances, the loop antenna can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can then be passed through the substrate 230 to the controller 250.

Figure 2D:
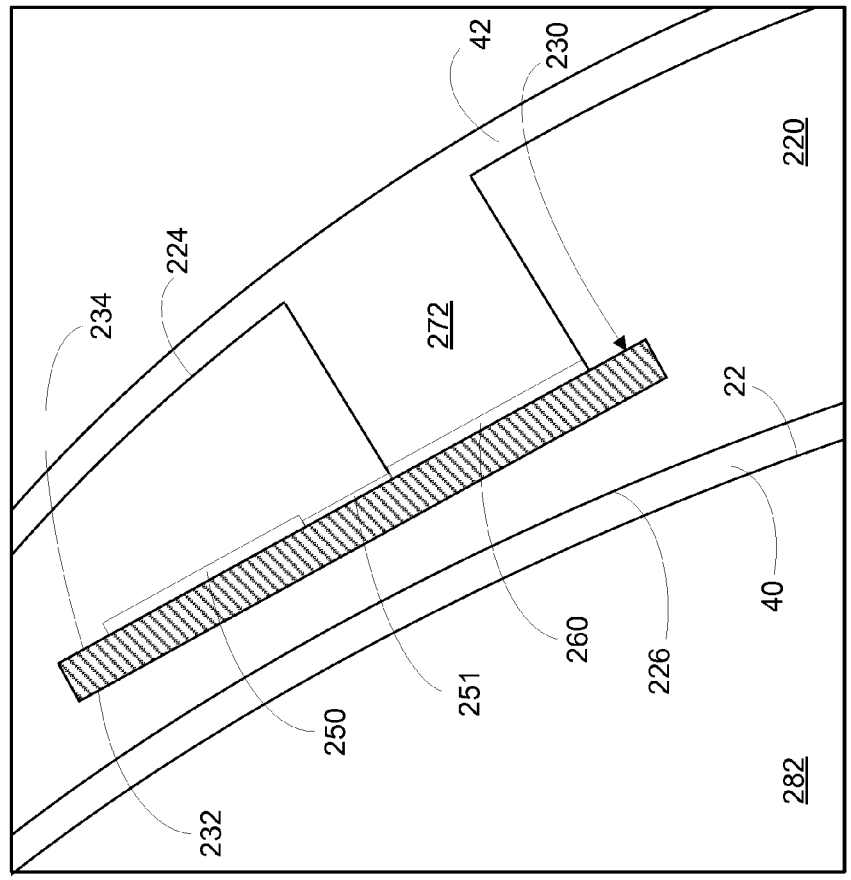
FIG. 2D is a side cross-section view enhanced to show the tear film layers surrounding the surfaces of the example eye-mountable device when mounted as shown in FIG. 2C, in accordance with an example embodiment.
Figure 2C:
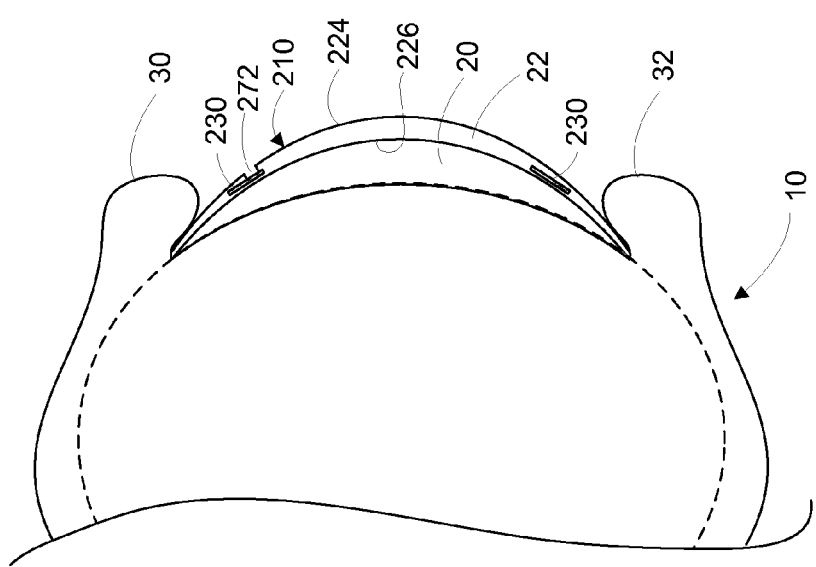
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the convex surface 224. As described above, the substrate 230 is a flattened ring with an inward-facing surface 232 (facing concave surface 226 of the polymeric material 220) and an outward-facing surface 234 (facing convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the outward-facing surface 234 such that the bio-interactive electronics 260 are facing convex surface 224.

The polymer layer defining the anterior side may be greater than 50 micrometers thick, whereas the polymer layer defining the posterior side may be less than 150 micrometers. Thus, bio-interactive electronics 260 may be at least 50 micrometers away from the convex surface 224 and may be a greater distance away from the concave surface 226. However, in other examples, the bio-interactive electronics 260 may be mounted on the inward-facing surface 232 of the substrate 230 such that the bio-interactive electronics 260 are facing concave surface 226. The bio-interactive electronics 260 could also be positioned closer to the concave surface 226 than the convex surface 224. With this arrangement, the bio-interactive electronics 160 can receive analyte concentrations in the tear film 292 through the channel 272.

Figure 3:
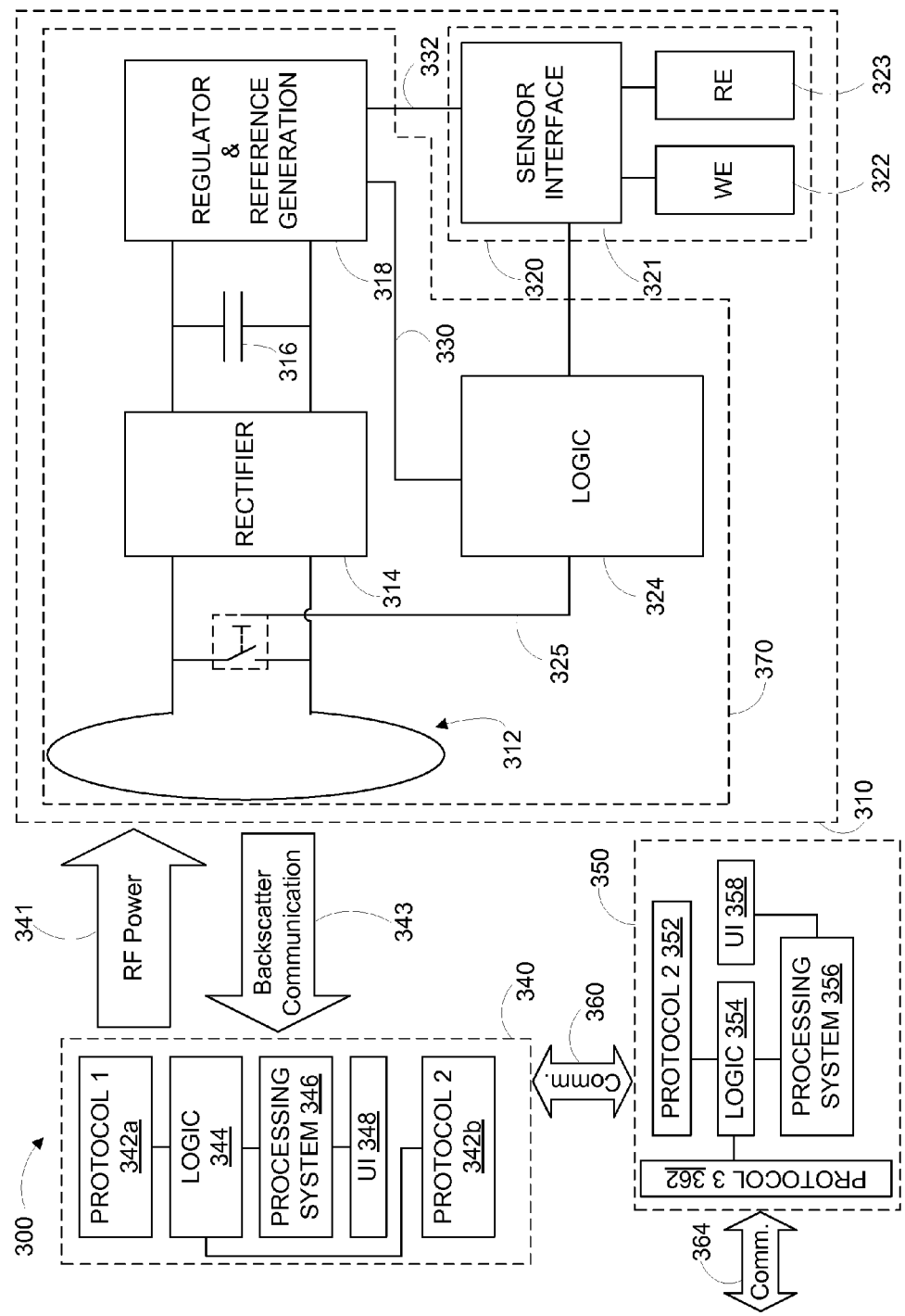
FIG. 3 is a functional block diagram of an example system for electrochemically measuring a tear film analyte concentration, in accordance with an example embodiment.

FIG. 3 is a functional block diagram of a system 300 for electrochemically measuring and displaying a tear film analyte concentration. The system 300 includes an eye-mountable device 310 with embedded electronic components in communication with and powered by reader 340. Reader 340 can also be configured to communicate with display device 350. Reader 340 and eye-mountable device 310 can communicate according to one communication protocol or standard, shown in FIG. 3 as Protocol 1, and reader 340 and display device 350 can communicate according to one communication protocol or standard, shown in FIG. 3 as Protocol 2. In some embodiments, Protocol 1 and Protocol 2 are the same; while in other embodiments, Protocol 1 differs from Protocol 2. In particular embodiments, Protocol 1 is an RFID protocol and Protocol 2 is either a Bluetooth protocol, Wi-Fi protocol, or ZigBee protocol. In other particular embodiments, Protocol 1 is either a Bluetooth protocol, a Wi-Fi protocol, or a ZigBee protocol. In still other particular embodiments, Protocol 2 is a wired protocol; such as, but not limited to, a Universal Serial Bus protocol, a Registered Jack protocol (e.g., RJ-25), or a wired Local Area Network protocol (e.g., Ethernet).

The eye-mountable device 310 includes an antenna 312 for capturing radio frequency (RF) power 341 from the reader 340. In some embodiments, RF power 341 and/or backscatter communication 343 can be provided in accordance with a communications standard or protocol, such as Protocol 1 shown in FIG. 3.

The eye-mountable device 310 includes rectifier 314, energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the reader 340 by modulating the impedance of the antenna 312. An impedance modulator 325 (shown symbolically as a switch in FIG. 3) can be used to modulate the antenna impedance according to instructions from the hardware logic 324. Similar to the eye-mountable device 110 shown in FIG. 1 and the eye-mountable device 210 shown in FIG. 2, the eye-mountable device 310 can include a mounting substrate embedded within a polymeric material configured to be mounted to an eye.

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received RF power 341. RF power 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the RF power 341 from the reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance are detected by the reader 340 via the backscatter signal 343.

Reader 340 can include Protocol 1 front end 342a and logic components 344 to communicate using Protocol 1, decode the information indicated by the backscatter signal 343, provide digital inputs to a processing system 346 and receive inputs and/or provide outputs via user interface 348. Protocol 1 can be, for example, an RFID protocol. In some embodiments, part or all of eye-mountable device 310 can be configured to perform some or all features of an RFID tag. For example, as shown in FIG. 3, some or all of the components shown as tag 370 of eye-mountable device 210 can perform some or all features of an RFID tag; e.g., antenna 312, rectifier 314, energy storage 316, voltage regulator 318, hardware logic 324, etc.

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

A processing system, such as, but not limited to, processing system 346 or processing system 356, can include one or more processors and one or more storage components. Example processor(s) include, but are not limited to, CPUs, Graphics Processing Units (GPUs), digital signal processors (DSPs), application specific integrated circuits (ASICs). Example storage component(s) include, but are not limited to volatile and/or non-volatile storage components, e.g., optical, magnetic, organic or other memory, disc storage; Random Access Memory (RAM), Read-Only Memory (ROM), flash memory, optical memory unit, and disc memory. The storage component(s) can be configured to store software and data; e.g., computer-readable instructions configured, when executed by a processor of the processing system, to cause the processing system to carry out functions such as but not limited to the herein-described functions of reader 340, eye-mountable device 310, and/or display device 350.

The reader 340 can associate the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or an external memory (e.g., by communicating with the external memory either on display device 350 or through a network).

User interface 348 of reader 340 can include an indicator, such as but not limited to one or more light-emitting diodes (LEDs), that can indicate that reader 340 is operating and provide some information about its status. For example, reader 340 can be configured with an LED that displays one color (e.g., green) when operating normally and another color (e.g., red) when operating abnormally. In other embodiments, the LED(s) can change display when processing and/or communicating data in comparison to when idle (e.g., periodically turn on and off while processing data, constantly stay on or constantly stay off while idle).

In some embodiments, one or more of the LED(s) of user interface 348 can indicate a status of sensor data; e.g., not display when sensor data are either within normal range(s) or unavailable, display in a first color when sensor data are either outside normal range(s) but not extremely high or low, and display a second color when the sensor data are extremely high and/or low. For example, if sensor data indicate that blood-glucose levels are extremely high or low, user interface 348 can be instructed by processing system 346 to display using the second color. In particular embodiments, user interface 348 can include a speaker or other sound-emitting device to permit reader 340 to generate sounds; e.g., warning sound(s) and/or tone(s) if sensor data are extremely high and/or low.

In some embodiments, reader 340 can have one or more buttons and/or other devices to receive inputs. For example, reader 340 can have a calibration button to indicate when calibration data is to be generated.

In some embodiments, reader 340 can communicate with devices in addition to eye-mountable device 310/tag 370. For example, FIG. 3 shows communication 360 between reader 340 and display device 350 using Protocol 2.

To communicate with display device 350, reader 340 can include Protocol 2 front end 342b and hardware logic 344 can be configured to use Protocol 2 front end 342b to communicate using Protocol 2. In some embodiments, processing system 346 can be configured to include and/or perform the herein-described functionality of hardware logic 344.

FIG. 3 shows that display device 350 can include Protocol 2 front end 352, hardware logic 354, processing system 356, and user interface (UI) 358. Hardware logic 354 can be configured to use Protocol 2 front end 352 to communicate using Protocol 2 with at least reader 340. Processing system 356 can include computer-readable instructions that, when executed, are configured to perform some or all the herein-described functions of display system 350. In some embodiments, processing system 356 can be configured to include and/or perform the herein-described functionality of hardware logic 354. UI 358 can be configured with hardware and/or software configured to present images, text, sound, haptic feedback, etc., such as, but not including, presenting images, text, audio, and/or video information related to data received from reader 180 as part of communication 360.

In some embodiments, display device 350 can include Protocol 3 front end 362. In these embodiments, hardware logic 354 can be configured to use Protocol 3 front end 362 to for sending and receiving communications 364 using Protocol 3 with one or more other devices (not shown in FIG. 3). Protocol 3 can include one or more wireless protocols, such as, but not limited to, a RFID protocol, a Bluetooth protocol, a Wi-Fi protocol, a ZigBee protocol, a WiMax protocol, or a Wireless Wide Area Network protocol (e.g., TDMA, CDMA, GSM, UMTS, EV-DO, LTE) and/or one or more wired protocols; such as, but not limited to, a Universal Serial Bus protocol, a Registered Jack protocol (e.g., RJ-25), or a wired Local Area Network protocol (e.g., Ethernet). In particular of these embodiments, Protocol 2 front end 352 and Protocol 3 front end 362 can be combined.

In embodiments utilizing Protocol 3, display device 350 can be used to forward and/or bridge data with the one or more other devices. In particular of these embodiments, a device of the one or more other devices can be a server configured to run one or more applications for collecting data from display device 350; e.g., a cloud data collection application.

III. Example Potentiostat

Figure 4:
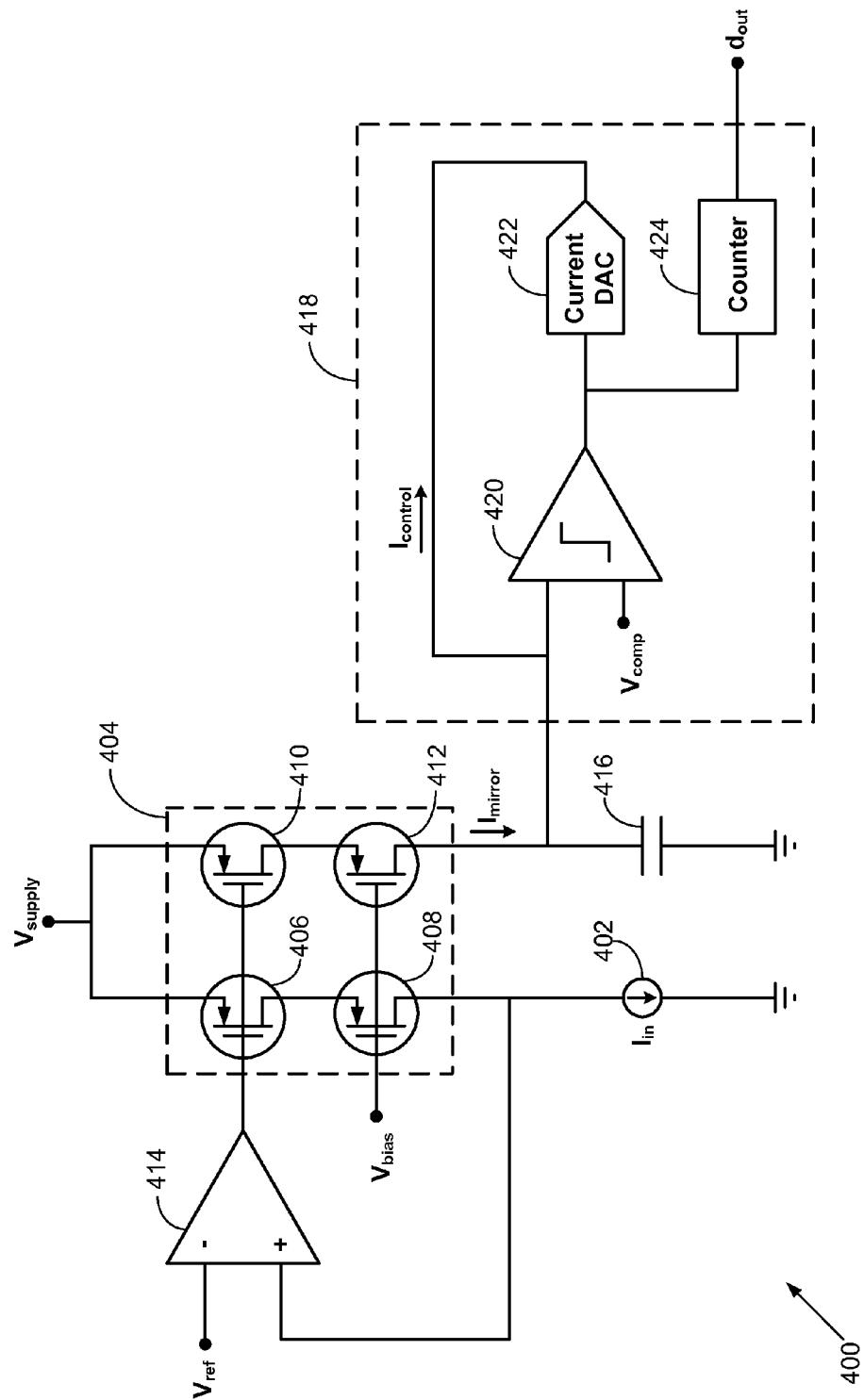
FIG. 4 is a schematic diagram of a potentiostat, in accordance with an example embodiment.

FIG. 4 schematically illustrates an example potentiostat 400. Potentiostat 400 could, for example, correspond to or be included in sensor interface 152 shown in FIG. 1 or sensor interface 321 shown in FIG. 3. Thus, potentiostat 400 could be part of a body-mountable device, such as an eye-mountable device. Alternatively, potentiostat 400 could be included in some other type of device or system.

Potentiostat 400 can function to maintain a desired voltage on a working electrode (e.g., relative to a reference electrode)

of an electrochemical sensor while also measuring an input current through the working electrode. The input current may result from oxidation or reduction reactions related to an analyte. In FIG. 4, the working electrode is represented as a current source 402 of the input current ($I_{in}$). The "ground" in potentiostat 400 could, thus, correspond to the reference electrode.

Potentiostat 400 includes a current mirror 404 coupled to the working electrode (current source 402). The current mirror 404 is configured to develop a mirror current ($I_{mirror}$) that mirrors the input current ($I_{in}$). The mirror current is related to the input current such that changes in the input current are reflected by changes in the mirror current. In some examples, the mirror current is approximately equal to the input current. In other examples, the mirror current is equal to the input current multiplied by a scaling factor and/or with the addition of a fixed offset. As shown, current mirror 404 includes two current paths connected to a supply voltage ($V_{supply}$). The input current flows through a first current path, and the mirror current flows through a second current path. In this example, the first current path includes field-effect transistors 406 and 408 connected in series, and the second current path includes field-effect transistors 410 and 412 connected in series. It is to be understood, however, that this configuration of current mirror 404 is merely one possible example. In general, current mirror 404 could include a greater or fewer number of transistors in each current path, and the transistors could be field-effect transistors or some other type of transistor.

Potentiostat 400 also includes a voltage regulator configured to maintain a voltage on the working electrode based on a reference voltage ($V_{ref}$). As shown, the voltage regulator is in the form of a differential amplifier 414. The differential amplifier 414 has an inverting input connected to the reference voltage ($V_{ref}$) and a non-inverting input connected to the working electrode (current source 402). The output of the differential amplifier 414 is connected to the gate of field-effect transistor 406 and the gate of field-effect transistor 410. The gates of field-effect transistors 408 and 412 are connected to a fixed bias voltage ($V_{bias}$). In this way, the output of differential amplifier 414, in combination with the fixed bias voltage ($V_{bias}$), controls the current mirror 404 such that the voltage at the working electrode is equal (or nearly equal) to the reference voltage ($V_{ref}$).

Figure 5:
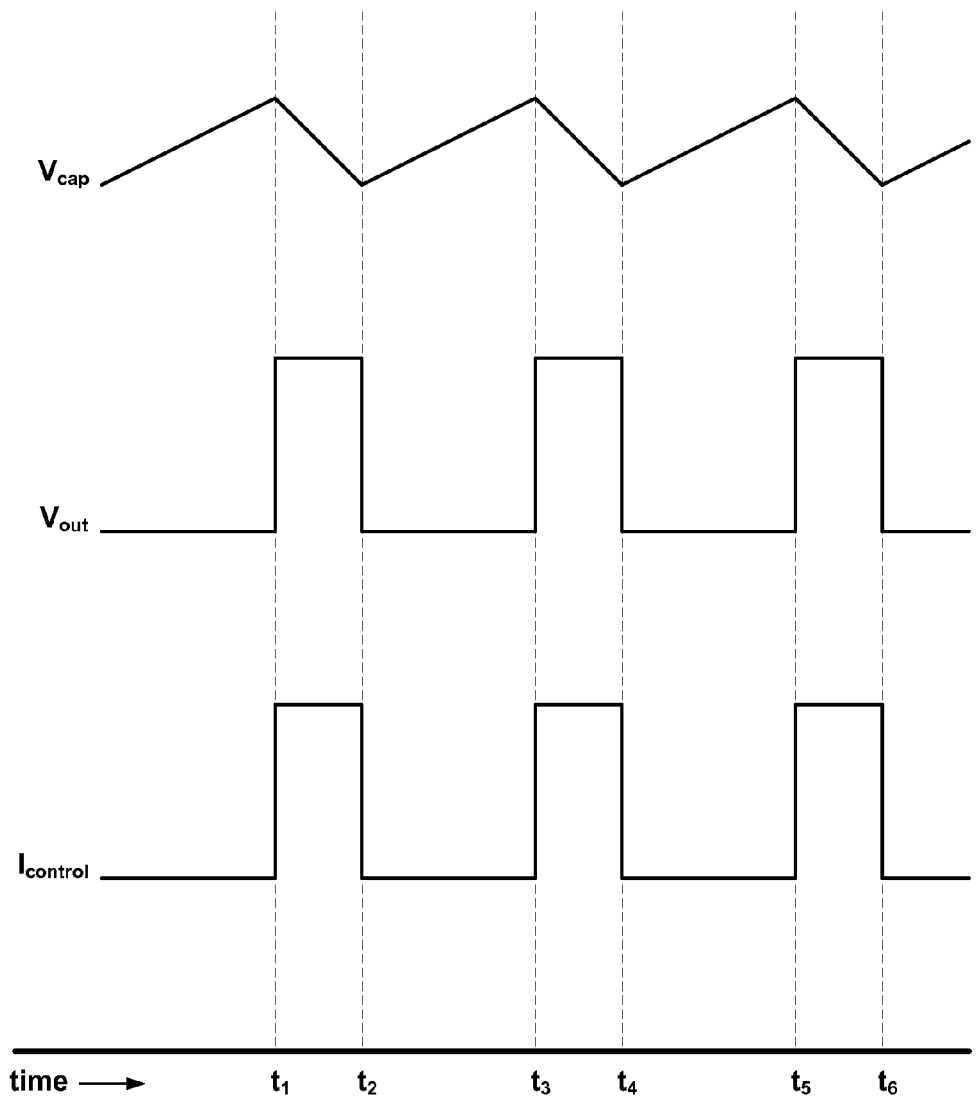
FIG. 5 shows variations of a capacitor voltage, waveform output by a comparator, and control current as a function of time, in accordance with an example embodiment.

In potentiostat 400, the mirror current ($I_{mirror}$) is integrated by a passive integrator, which is shown in FIG. 4 as a capacitor 416. Thus, when capacitor 416 is being charged by the mirror current, the voltage across the capacitor increases at a rate that is related to the magnitude of the mirror current. As discussed in more detail below, capacitor 416 can also be discharged by a control current ($I_{control}$). When capacitor 416 is being discharged by the control current, the voltage across the capacitor decreases at a rate that is related to the difference between the magnitude of the control current and the magnitude of the mirror current. With alternating periods of charging and discharging of capacitor 416, the capacitor voltage ($V_{cap}$) fluctuates in a sawtooth pattern, as shown in FIG. 5.

Potentiostat 400 also includes a sigma-delta analog-to-digital converter 418, which produces a digital output ($d_{out}$) that is representative of the magnitude of the mirror current ($I_{mirror}$) and, hence, the magnitude of the input current ($I_{in}$). As shown, sigma-delta analog-to-digital converter 418 includes a comparator 420, a current source 422, and a counter 424.

Comparator 420 has one input that is coupled to capacitor 416 and another input that is coupled to a comparison voltage ($V_{comp}$). The comparison voltage could be, for example, equal to the reference voltage ($V_{ref}$). With this arrangement, comparator 420 is configured to output a waveform based on variations of the capacitor voltage ($V_{cap}$) relative to the comparison voltage ($V_{comp}$). The waveform may alternate between a first voltage level (e.g., a logic low level) and a second voltage level (e.g., a logic high level). When the capacitor voltage ($V_{cap}$) increases to a level above the comparison voltage ($V_{comp}$), the output of comparator 420 may transition from the first voltage level to the second voltage level. When the capacitor voltage ($V_{cap}$) decreases to a level below the comparison voltage ($V_{comp}$), the output of comparator 420 may transition from the second voltage level to the first voltage level. FIG. 5 shows an example of how the voltage output ($V_{out}$) from comparator 420 may vary in response to variations of the capacitor voltage ($V_{cap}$).

Current source 422 and counter 424 receive as input the waveform that is output by comparator 420. Current source 422 is configured to provide the control current ($I_{control}$) based on the waveform. In an example, current source 422 is a one-bit, current digital-to-analog converter. Thus, current source 422 may alternate the control current between a first current level and a second current level with a duty cycle that is based on the waveform output from comparator 420. The first current level may be a low current level (e.g., zero current) that current source 422 provides when the waveform output from comparator 420 is at a first voltage level (e.g., a logic low level). The second current level may be a high current level ($I_{high}$) that current source 422 provides when the waveform output from comparator 420 is at a second voltage level (e.g., a logic high level).

FIG. 5 illustrates an example in which the control current ($I_{control}$) varies between a low level ($I_{control}=0$) and a high level ($I_{control}=I_{high}$), in response to variations in $V_{out}$ output of comparator 420), which, in turn, is based on variations of $V_{cap}$ (the voltage across capacitor 416). When $I_{control}$ is zero (and $V_{out}$ is at a low level), capacitor 416 is charged by $I_{mirror}$, and $V_{cap}$ increases at a rate related to the magnitude of $I_{mirror}$. $V_{cap}$ increases until it reaches a level above $V_{comp}$ that causes $V_{out}$ to transition from the low level to the high level. FIG. 5 shows such transitions occurring at times $t_1$, $t_3$, and $t_5$. The transition of $V_{out}$ from the low level to the high level causes the control current to increase to the high level ($I_{control}=I_{high}$). This, in turn, causes capacitor 416 to discharge. Thus, $V_{cap}$ decreases at a rate related to the difference in magnitude between the control current and the mirror current ($I_{high}-I_{mirror}$). $V_{cap}$ decreases until it reaches a level below $V_{comp}$ that causes $V_{out}$ to transition from the high level to the low level. FIG. 5 shows such transitions occurring at times $t_2$, $t_4$, and $t_6$. The transition of $V_{out}$ from the high level to the low level causes the control current to decrease to the low level ($I_{control}=0$).

With the control current ($I_{control}$) varying between zero and $I_{high}$, as shown in FIG. 5, the time-average value of the control current ($I_{control}$) will be equal to the mirror current ($I_{mirror}$) and, hence, related to the input current ($I_{in}$) from the working electrode. To measure the time-average value of the control current, counter 424 is configured to detect a particular feature in the waveform ($V_{out}$) generated by comparator 420, such as upward transitions or downward transitions in the waveform, and count the number of time the particular feature in the waveform occurs during a predetermined sampling period. The predetermined sampling period could be any period of time during which the input current from the working electrode and, hence, the mirror current is relatively stable. In some examples, the predetermined sampling period could be between 0.01 and 1.0 seconds. For example, the predetermined sampling period could be 0.1 seconds.

The digital output ($d_{out}$) provided by counter 424 may correspond to the count at the end of the predetermined sampling period. In this way, the value of $d_{out}$ is representative of the magnitude of the mirror current ($I_{mirror}$) and, hence, the input current ($I_{in}$) from the working electrode. Assuming that $I_{in}$ is equal to $I_{mirror}$, then the relationship between $d_{out}$ and $I_{in}$ is dependent on the maximum possible digital output ($d_{max}$) and the value of the high level of the control current ($I_{high}$) as follows: $I_{in}=(d_{out}/d_{max})I_{high}$.

It is to be understood, however, that the above relationship between $I_{in}$ and $I_{high}$ is only one possible example. For example, current source 422 could be a return-to-zero (RTZ) DAC. In that case, for a logic high input, the RTZ DAC produces a current pulse that starts at a low level (e.g., zero), goes to a high level ($I_{high}$), and then back to the low level, with a particular duty cycle (D). Thus, the time-average value of $I_{control}$ (which corresponds to $I_{mirror}$) for the maximum possible digital output ($d_{max}$) would be equal to high current level ($I_{high}$) multiplied by the DAC duty cycle (D). In this example implementation, assuming that $I_{in}$ is equal to $I_{mirror}$, then the relationship between $d_{out}$ and $I_{in}$ is as follows: $I_{in}=D(d_{out}/d_{max})I_{high}$.

In some examples, $I_{mirror}$ is not equal to $I_{in}$ but, rather, is systematically larger than $I_{in}$ or smaller than $I_{in}$. For example, current mirror 404 could be designed such that the mirror current ($I_{mirror}$) is equal to the input current ($I_{in}$) multiplied by a scaling factor (s). In some implementations, s could be less than one (s<1), for example, to reduce power consumption. In other implementations, s could be greater than one (s>1), for example, to increase the precision of the measurement.

The digital output ($d_{out}$) from counter 424 can be provided to other components, for example, to calculate a concentration of an analyte, such as glucose. For example, with potentiostat 400 corresponding to sensor interface 321 shown in FIG. 3, logic circuit 324 may receive the digital output ($d_{out}$) and modulate the impedance of antenna 312 to communicate the digital output to reader 340. Reader 340 may then calculate an analyte concentration based on the digital output. Alternatively, reader 340 may communicate the digital output to display device 350, and display device 350 may calculate an analyte concentration based on the digital output.

IV. Example Operations

Figure 6:
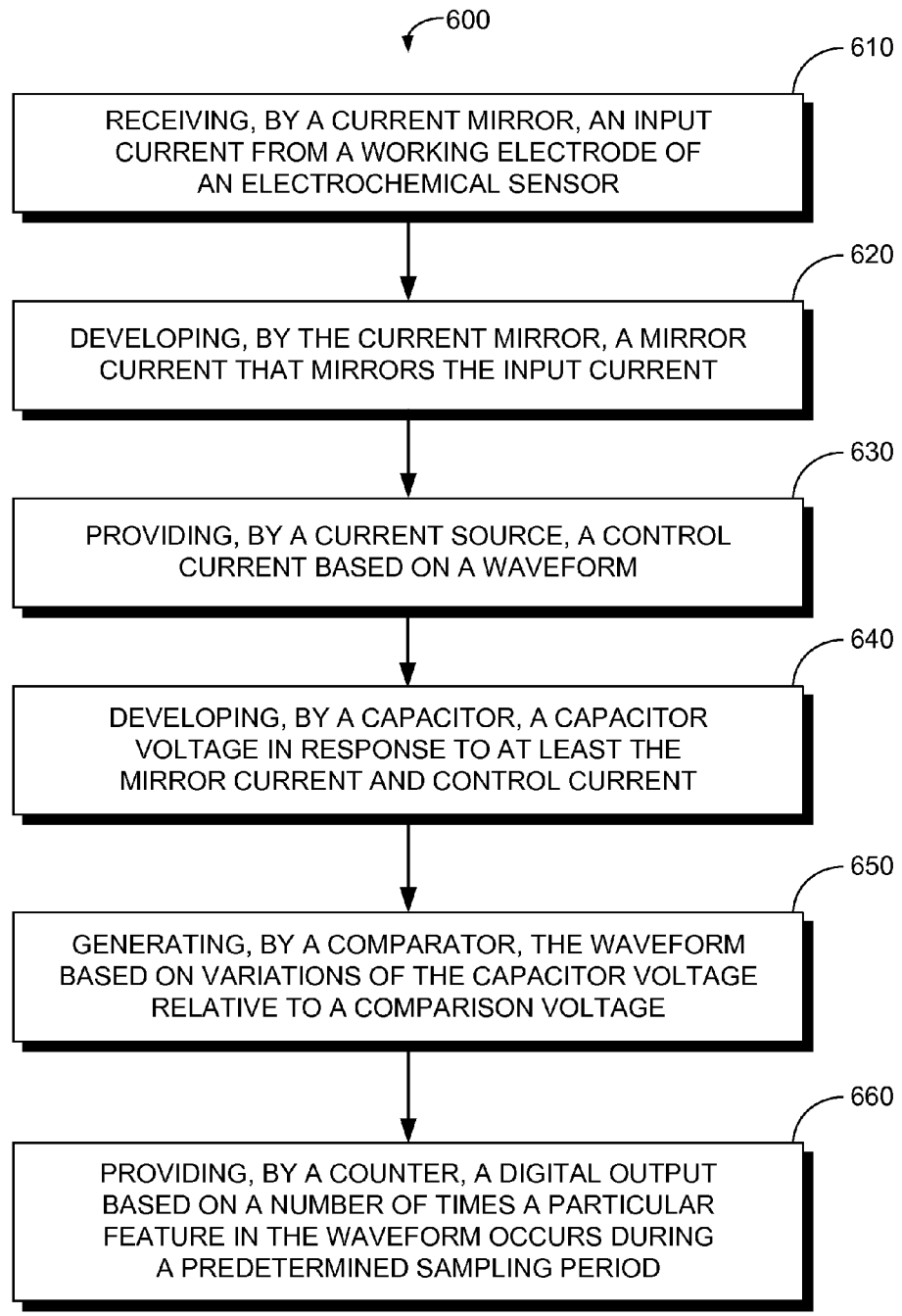
FIG. 6 is a flow chart of an example method, in accordance with an example embodiment.

FIG. 6 is a flow chart of an example method 600. Method 600 can correspond to operations performed by a potentiostat, such as potentiostat 400 shown in FIG. 4 and described above.

Method 600 can begin at block 610. At block 610, a current mirror (e.g., current mirror 404) receives an input current from a working electrode of an electrochemical sensor. The input current could be from an oxidation or reduction reaction related to an analyte in a fluid to which the electrochemical sensor is exposed. Thus, a measurement of the input current may be related to the concentration of the analyte in the fluid.

At block 620, the current mirror develops a mirror current that mirrors the input current. The mirror current could be equal or substantially equal (e.g., equal to within the resolution of the measurement process) to the input current. Alternatively, the mirror current could differ from the input current by a fixed offset and/or scaling factor, which could be determined in a separate calibration process. Thus, there may be a known relationship between the input current and mirror current.

At block 630, a current source provides a control current based on a waveform. In an example, the current source could be a one-bit current DAC, such as current source 422 shown in FIG. 4. The waveform could alternate between a logic low level, which causes the current source to provide the control current at a first level (e.g., zero current), and a logic high level, which causes the current source to provide the control current at a second level (e.g., $I_{high}$).

FIG. 5 illustrates an example relationship between a waveform ($V_{out}$) and a control current ($I_{control}$). It is to be understood, however, that the waveform and/or control current could vary in other ways. In addition, the current source could be configured other than as a one-bit current DAC.

At block 640, a capacitor (e.g., capacitor 416) develops a capacitor voltage in response to at least the mirror current and control current. In an example, the mirror current and control current may cause the capacitor voltage to fluctuate in a sawtooth pattern, as shown in FIG. 5. In this example, the capacitor develops an increasing capacitor voltage during a first period of time, as a result of the capacitor being charged by the mirror current, and develops a decreasing capacitor voltage during a second period of time, as a result of the capacitor being discharged by the control current.

At block 650, a comparator (e.g., comparator 420) generates the waveform based on variations of the capacitor voltage relative to a comparison voltage. FIG. 5 illustrates an example relationship between the capacitor voltage ($V_{cap}$) and the waveform generated by the comparator ($V_{out}$). In this example, the waveform varies between a first voltage level (e.g., a logic low level) and a second voltage level (e.g., a logic high level), with the comparator transitioning from the first voltage level to the second voltage level when the capacitor voltage increases to a level above the comparison voltage and transitioning from the second voltage level to the first voltage level when the capacitor voltage decreases to a level below the comparison voltage.

At block 660, a counter (e.g., counter 424) provides a digital output based on a number of times a particular feature in the waveform occurs during a predetermined sampling period. In the case that the waveform varies between a first voltage level and a second voltage level, the particular feature in the waveform could be either an upward transition from the first voltage level to the second voltage level or a downward transition from the second voltage level to the first voltage level. The counter may detect each such upward or downward transition and, in response, increment a count of the number of such transitions. In this way, the counter may count the number of upward or downward transitions occurring during the predetermined sampling period and, at the end of the predetermined sampling period, provide a digital output based on the count. The digital output may, thus, be representative of the magnitude of the mirror current and, hence, the input current from the working electrode.

In some examples, method 600 may further involve a voltage regulator maintaining a voltage on the working electrode based on a reference voltage ($V_{ref}$). The voltage regulator could be, for example, a differential amplifier with an inverting input connected to the reference input, a non-inverting input connected to the working electrode, and an output connected to the current mirror. The output controls the current mirror such the voltage at the working electrode is substantially equal to the reference voltage (e.g., equal to within the limitations of the finite gain and input offset of the differential amplifier). For example, as shown in FIG. 4, differential amplifier 414 controls current mirror 404 by providing an output to the gates of field-effect transistors 406 and 410.

In examples in which the voltage regulator maintains a voltage on the working electrode that is substantially equal to the reference voltage ($V_{ref}$), the comparison voltage used by the comparator may also be substantially equal to the reference voltage ($V_{ref}$). Thus, the voltage on the working electrode may be fixed at $V_{ref}$ while the capacitor voltage ($V_{cap}$) fluctuates between a level above $V_{ref}$ and a level below $V_{ref}$ as a result of the measurement process. The fluctuations may be small relative to $V_{ref}$. Moreover, the current mirror may shield the working electrode from the fluctuations in the capacitor voltage ($V_{cap}$).

V. Conclusion

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

Further, where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

In situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from a content server that may be more relevant to the user. In addition, certain data may be treated in one or more ways before it is stored or used, so that personally identifiable information is removed. For example, a user's identity may be treated so that no personally identifiable information can be determined for the user. Thus, the user may have control over how information is about the user is collected and used.

What is claimed is:

1. A system, comprising:
   a working electrode of an electrochemical sensor, wherein the working electrode is configured to develop an input current;
   a capacitor;
   a current mirror coupled to the working electrode, wherein the current mirror comprises a first current path between a voltage supply and the working electrode, a second current path between the voltage supply and the capacitor, a first field-effect transistor and a second field-effect transistor connected in series in the first current path, and a third field-effect transistor and a fourth field-effect transistor connected in series in the second current path, wherein the current mirror is configured to develop a mirror current that mirrors the input current;
   a voltage regulator coupled to the working electrode and current mirror, wherein the voltage regulator is configured to maintain a voltage on the working electrode based on a reference voltage, wherein the voltage regulator comprises a differential amplifier having an inverting input connected to the reference voltage, a non-inverting input connected to the working electrode, and an output connected to a gate of the first field-effect transistor and a gate of the third field-effect transistor;
   a current source configured to provide a control current, wherein the capacitor is configured to develop a capacitor voltage in response to at least the mirror current and control current;
   a comparator coupled to the capacitor, wherein the comparator is configured to output a waveform based on variations of the capacitor voltage relative to a comparison voltage; and
   a counter coupled to the comparator, wherein the counter is configured to detect a particular feature in the waveform output from the comparator and to provide a digital output based on a number of times the particular feature in the waveform occurs during a predetermined sampling period.

2. The system of claim 1, wherein the current source is coupled to the comparator and is configured to provide the control current based on the waveform output from the comparator.

3. The system of claim 2, wherein the current source is configured to alternate the control current between a first current level and a second current level with a duty cycle based on the waveform output from the comparator.

4. The system of claim 3, wherein the comparator is configured to output the waveform between a first voltage level and a second voltage level, such that the waveform transitions from the first voltage level to the second voltage level when the capacitor voltage increases to a level above the comparison voltage and transitions from the second voltage level to the first voltage level when the capacitor voltage decreases to a level below the comparison voltage.

5. The system of claim 4, wherein the comparison voltage is equal to the reference voltage.

6. The system of claim 4, wherein the current source is configured to provide the control current at the first current level when the waveform is at the first voltage level and to provide the control current at the second current level when the waveform is at the second voltage level.

7. The system of claim 6, wherein the control current at the first current level is sufficient to allow the capacitor to charge up such that the capacitor voltage increases at a rate related to the mirror current, and wherein the control current at the second current level is sufficient to cause the capacitor to discharge such that the capacitor voltage decreases.

8. The system of claim 6, wherein the current source comprises a digital-to-analog converter.

9. The system of claim 4, wherein the particular feature is a transition from the first voltage level to the second voltage level in the waveform.

10. The system of claim 1, wherein the predetermined sampling period is between 0.01 and 1.0 seconds.

* * * * *